United States Patent
DeJonge

(10) Patent No.: US 6,173,868 B1
(45) Date of Patent: Jan. 16, 2001

(54) NASAL SPRAYER WITH FOLDING ACTUATOR

(75) Inventor: Stuart DeJonge, Easton, PA (US)

(73) Assignee: Calmar Inc., City of Industry, CA (US)

( * ) Notice: Under 35 U.S.C. 154(b), the term of this patent shall be extended for 0 days.

(21) Appl. No.: 09/521,622

(22) Filed: Mar. 8, 2000

(51) Int. Cl.[7] .................................................. B65D 88/54
(52) U.S. Cl. ................................ 222/321.6; 222/153.13; 604/192
(58) Field of Search ......................... 222/153.13, 153.14, 222/321.6, 465.1, 466, 470; 604/94.01, 162, 187, 192, 198, 263

(56) References Cited

U.S. PATENT DOCUMENTS

| | | |
|---|---|---|
| 4,640,443 | 2/1987 | Corsette . |
| 4,944,429 | 7/1990 | Bishop et al. . |
| 5,215,227 * | 6/1993 | Farner ................................ 222/321.6 |
| 5,894,963 * | 4/1999 | Hirota ................................. 222/321.6 |
| 6,092,692 * | 4/1999 | Riskin ................................. 222/321.6 |

* cited by examiner

*Primary Examiner*—Kevin Shaver
*Assistant Examiner*—Thach H Bui
(74) *Attorney, Agent, or Firm*—Dykema Gossett PLLC

(57) ABSTRACT

A nasal pump sprayer having a folding actuator that can be used as a dust cover, finger grip and shipping clip. The folding actuator has a pair of wings that are hingedly connected to the pump body of the nasal pump sprayer and which can be locked in a closed position and used as a cover and shipping stop. The wings may also be opened to a lateral position and used as finger grips for actuating the nasal pump sprayer. Each wing has a locking means at one end for snap-locking the wings together and a hollow interior that is complementary in shape to the nozzle of the sprayer. An immobilizing means extends from the connected end of each wing and engages a confronting edge of the pump body thus locking the plunger head of the nasal pump sprayer against reciprocation for storage and shipping.

8 Claims, 1 Drawing Sheet

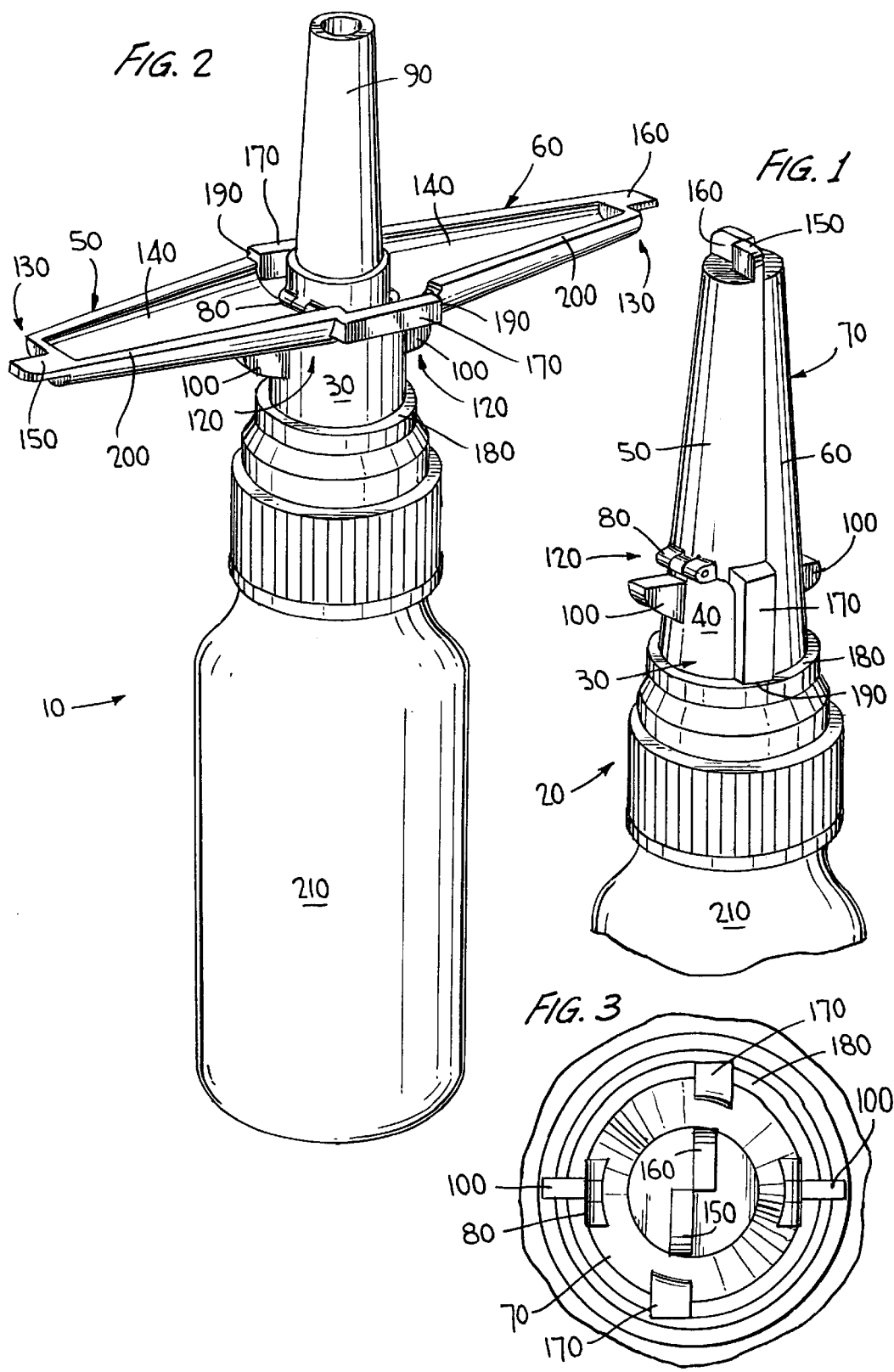

NASAL SPRAYER WITH FOLDING ACTUATOR

BACKGROUND OF THE INVENTION

This invention relates generally to a manually operated pump nasal sprayer and more particularly to a nasal sprayer having a folding actuator mounted on the sprayer that can be used as a dust cover and a shipping clip preventing actuation during shipping and storage when in the closed position, and can be used as a finger grip when in the open position.

Covers for manually operated pump nasal sprayers are needed to keep the nasal adaptor of the sprayer clean and free from unwanted dust, dirt and bacteria. A nasal sprayer having a folding actuator can be multi-functional having various applications, such as a dust cover, a shipping clip and a finger grip. While there are numerous mechanisms in the art that have separate covers for a nasal adaptor, none are multi-purpose and versatile enough to be useful in both an open and closed position for different functions.

Generally, dust covers and actuators for nasal pump sprayers are separate elements wherein the dust covers are cup-like caps and are snapped on or screwed on the sprayer such as those shown in U.S. Pat. No. 4,944,429 entitled "Manually-Operable Spray Dispenser With Locking Mechanism", issued to Bishop et al. The dust cover in the Bishop patent is a cup-like cap mounted on the winged actuator and the actuator is mounted on the screw cap of the sprayer. The separateness of each element requires a certain agility and effort in removing the cover from the sprayer. Moreover, the user must keep track of the cover, while using the sprayer, so the cover is not misplaced, dropped or contaminated. It is generally more expensive to manufacture separate, distinct parts as opposed to a single part. Covers like those shown in the Bishop patent may achieve their stated objectives, however it is desirable to have a cover that is multi-functional, yet economical, easy to manufacture and assemble and easy to use.

SUMMARY OF THE INVENTION

It is an object of the present invention to provide a cover to prevent dust and other unnecessary debris from coming into contact with the nasal adaptor or nozzle of a nasal pump sprayer.

Another object of the present invention is to provide a cover that can be used as a shipping clip for the nasal pump sprayer when the sprayer is transported.

Yet another object of the present invention is to provide a cover for a nasal pump sprayer that can be used as a finger grip to aid the user in gripping the sprayer when in use.

Still another advantage of the present invention is to provide a cover that is maintained on the sprayer at all times and as such, is not prone to being lost or misplaced by the user.

According to the invention, the nasal pump sprayer has a pump body with an upstanding elongated discharge nozzle that extends from a reciprocating plunger head. The nasal pump sprayer also has an actuating means comprising a pair of opposed wings extending laterally outwardly from and hinged to the plunger head and a pair of stop projections that form a support surface for the wings when they are in an open position. The wings are used as finger grips for reciprocating the plunger head when in the open position and are used as a dust cover and shipping clip to cover the nozzle when in the closed position.

The presently claimed invention may have other objects, advantages and novel features that will become more apparent from the following detailed description of the invention when taken in conjunction with the accompanying drawings.

BRIEF DESCRIPTION OF THE DRAWINGS

FIG. 1 is a perspective view of a folding actuator for a nasal pump sprayer according to the present invention, the wings of the actuator shown in a raised, closed position;

FIG. 2 is a perspective view of a folding actuator mounted on a nasal pump sprayer, the wings of the actuator are shown in a lowered, open position; and FIG. 3 is a top plan view of the folding actuator of FIG. 1, with the wings of the actuator shown in a raised, closed position.

DETAILED DESCRIPTION OF THE INVENTION

The folding actuator 70 of FIG. 1 is shown in a closed position with a nozzle of a nasal pump sprayer enclosed within a pair of wings 50,60. Each wing 50,60 is movably connected to the plunger head 30 with a hinge 80. The plunger head 30 is reciprocatingly in communication with the pump body 20 and the pump body 20 is connected to a container 210 in any known manner common to the art.

Located on opposite sides of the plunger head 30 are support projections 100 that protrude or extend out of plunger head 30 and create a support for each wing 50,60 to abut and press against when opened to a lateral position. In FIG. 1, each support projection 100 is integrally formed with the plunger head 30, however they can be formed as a separate element that is connected thereto.

Each wing 50,60 has an immobilizing means comprised of a pump stop 170 that protrudes from the respective wing 50,60. Each pump stop 170 overlies a sidewall 40 of the plunger head 30 and communicates with or engages a confronting upper edge 180 of the pump body 20 when the folding actuator 70 is in the closed position as shown in FIGS. 1 and 3. Each pump stop 170 is integrally formed on the hinged end 120 of each wing 50,60 and is adjacent the hinge 80 as shown in FIG. 3.

Each wing 50,60 of the folding actuator 70 is movable to an open position wherein it is positioned so that it extends outwardly, perpendicular to the discharge nozzle 90 of the pump sprayer 10 as shown in FIG. 2. When the wings 50,60 are in this open position, an edge 200 surrounding the perimeter of each wing 50,60 forms a finger platform for the user to grip when activating the nasal pump sprayer 10. Each wing 50,60 rests against a respective support projection 100 and presses against the support projection 100 when a user pushes on the wings 50,60 to actuate the nasal pump sprayer 10.

Each wing 50,60 is comprised of a half-shell that is complementary in shape to the nozzle 90. The hollowed interior 140 surrounds or overlaps opposing halves of the discharge nozzle 90 when the wings 50,60 are raised and provides a protective cover for the nasal pump sprayer 10 when it is not in use or is being transported. When each wing 50,60 is placed in an open position that is substantially perpendicular to the nozzle 90, the pump stop 170 extends on the side of the nozzle 90 where its free end 190 may or may not slightly abut the hinged end 120 of the opposite wing 50,60. That is, the free end 190 of pump stop 170 on wing 50 may slightly abut against the hinged end 120 of wing 60. And the free end 190 of pump stop 170 on wing 60 may slightly abut the hinged end 120 of wing 50. This abutting relationship provides additional support to the wings 50,60 when they are used as finger grips for actuating the nasal pump sprayer 10.

Each wing 50,60 also has a locking means comprised of a finger tab 150,160 integrally formed therewith at their respective free ends 130. The finger tabs 150,160 are used as a mechanism for locking the folding actuator 70 in a closed position and they may aid the user in opening the folding actuator 70 when the nasal pump sprayer is to be used.

When the folding actuator 70 is in a closed position, to open the nasal pump sprayer 10 of the present invention, the user holds the container 210 in one hand and grasps the finger tabs 150,160 between the thumb and forefinger of the opposite hand. By squeezing the finger tabs 150,160 between the thumb and forefinger in an offset fashion so that the thumb ultimately pushes against finger tab 150 while the forefinger presses against the other finger tab 160 which causes both finger tabs 150,160 to separate in directions opposite from one another. As each finger tab 150,160 is pushed in a direction opposite the other, their respective wings 50,60 are forced to rotate around their respective hinges 80 as they move from an upright, closed position to a laterally extending, open position. As the wings 50,60 are moved from their upright position to their lateral position, they come into communication with the support projections 100 that project out from the outer wall 40 of the plunger head 30.

To actuate the nasal pump sprayer 10, the user grasps the sprayer 10 between the thumb and two fingers. The user places the thumb under the bottom of the container 210 with the forefinger across one of the wings 50 and the middle finger across the other wing 60. The user then squeezes the fingers and thumb together. During this squeezing motion, the fingers apply pressure to the wings 50,60 which press against the support projections 100 on the plunger head 30. As force is applied to the support projections 100, the plunger head 30 is forced down within the pump body 20 causing spray to be ejected out of the discharge nozzle 90, as is known in the art.

When the pressure against the wings 50,60 is released, the plunger head 30 returns to its extended, starting position. To place the nasal pump sprayer 10 back into a closed position where it can be protected and transported, the wings 50,60 are raised until the edge 200 of one wing 50 abuts against the edge of the other wing 60 and the finger tabs 150,160 are adjacent one another. When the wings 50,60 are in the raised position, the pump stop 170 on each wing 50,60 extends alongside the sidewall 40 of the plunger head 30 with each of their free ends 190 engaging a confronting portion of the pump body 20 thus preventing the nasal pump sprayer 10 from being actuated and allowing it to be transported without threat of actuation during transit. While in the raised position, the wings 50,60 also provide a protective dust cover preventing dust and debris from contacting the discharge nozzle 90.

The present invention has been described in detail herein in view of one particular embodiment, however it is to be understood that the invention is not limited to this single embodiment, and that various changes and modifications are made possible without departing from the scope of the invention.

A foreseeable alternative embodiment may include different types of finger tabs for securing the wings in a closed position. Also the actuating/cover means could include a one-piece unit together with the plunger head with each wing being connected by a living hinge.

What is claimed is:

1. A nasal pump sprayer, comprising:

a pump body having a reciprocable plunger head from which an upstanding elongated discharge nozzle extends;

actuating means on said plunger head for reciprocating said nozzle, comprising a pair of opposing wings extending laterally outwardly from said nozzle, said wings being hinged to said nozzle for movement between said laterally extending position and a folded together position overlying opposing halves of said nozzle to thereby function as a cover in said overlying position.

2. The nasal pump sprayer according to claim 1, wherein:

immobilizing means on at least one of said wings engages a confronting portion of said pump body in only said folded together position for immobilizing the nozzle against reciprocation.

3. The nasal pump sprayer according to claim 2, wherein:

said immobilizing means comprises a projection extending from a lower end of said at least one of the wings and overlying a sidewall of said plunger head in said folded together position.

4. The nasal pump sprayer according to claim 1, wherein:

said wings comprise half-shells complementary in shape to that of said nozzle and having cooperating means at free ends thereof for snap-locking said half-shells together in said folded together position.

5. A combined dust cover and actuator for a nasal pump sprayer having a reciprocable elongated nozzle extending from a plunger head of the sprayer comprising:

a pair of hollow wings hingedly connected to a base portion of said plunger head for pivotal movement between an outwardly extending nozzle actuating position and a closed together position in which said nozzle is nested within said hollow wings.

6. The combined dust cover and actuator according to claim 5, wherein:

immobilizing means extending from a lower end of said wings engage a confronting edge of a pump body portion of the nasal pump sprayer in said closed together position for locking the plunger head against reciprocation.

7. The combined dust cover and actuator according to claim 5, wherein:

locking means on said wings are provided for snap-locking said wings in said closed together position.

8. The combined dust cover and actuator according to claim 5, wherein:

lateral projections on said plunger head are provided to support said wings in said outwardly extended position.

* * * * *